(12) United States Patent
Dresden

(10) Patent No.: US 6,416,513 B1
(45) Date of Patent: Jul. 9, 2002

(54) CONFIGURABLE ELECTRODE INSTRUMENT FOR USE IN LOOP ELECTRICAL EXCISION PROCEDURES

(76) Inventor: Scott Dresden, 10 Old Jackson Ave., #48, Hastings, NY (US) 10706

( * ) Notice: Subject to any disclaimer, the term of this patent is extended or adjusted under 35 U.S.C. 154(b) by 141 days.

(21) Appl. No.: 09/689,037

(22) Filed: Oct. 12, 2000

(51) Int. Cl.[7] ............................................... A61B 18/18
(52) U.S. Cl. ........................................ 606/45; 600/564
(58) Field of Search .............................. 606/41, 45, 47, 606/49; 600/564

(56) References Cited

U.S. PATENT DOCUMENTS

| | | | |
|---|---|---|---|
| 4,718,419 A | * | 1/1988 | Okada |
| 4,811,733 A | * | 3/1989 | Borsanyi et al. |
| 4,917,082 A | * | 4/1990 | Grossi et al. |
| 5,047,042 A | * | 9/1991 | Jerath ......................... 606/167 |
| 5,282,799 A | * | 2/1994 | Rydell |
| 5,318,564 A | * | 6/1994 | Eggers |
| 5,324,288 A | * | 6/1994 | Billings et al. |
| 5,437,665 A | * | 8/1995 | Munro |
| 5,554,159 A | * | 9/1996 | Fischer |
| 5,569,244 A | * | 10/1996 | Hahnen |
| 5,658,280 A | * | 8/1997 | Issa |
| 5,676,663 A | * | 10/1997 | Kim ............................. 606/45 |
| 5,733,283 A | * | 3/1998 | Malis et al. |
| 5,746,746 A | * | 5/1998 | Garito et al. |
| 5,800,482 A | * | 9/1998 | Pomeranz et al. |
| 5,836,947 A | * | 11/1998 | Fleischman et al. |
| 5,855,061 A | * | 1/1999 | Malis et al. |
| 5,895,417 A | * | 4/1999 | Pomeranz et al. |
| 5,951,550 A | * | 9/1999 | Shirley et al. ................. 606/45 |
| 5,971,994 A | * | 10/1999 | Fritzsch |
| 5,980,519 A | * | 11/1999 | Hahnen et al. |
| 5,984,920 A | * | 11/1999 | Steinbach |
| 6,015,415 A | * | 1/2000 | Avellanet |
| 6,071,282 A | | 1/2000 | Fleischman |
| 6,071,279 A | | 6/2000 | Whayne et al. |
| 6,176,858 B1 | * | 1/2001 | Dequesne et al. ............. 606/47 |
| 6,309,388 B1 | * | 10/2001 | Fowler ......................... 606/95 |
| 6,344,026 B1 | * | 2/2002 | Burbank et al. ............. 600/567 |

* cited by examiner

Primary Examiner—Linda C. M. Dvorak
Assistant Examiner—David M. Ruddy
(74) Attorney, Agent, or Firm—Dennis G. LaPointe; Mason & Associates, P.A.

(57) ABSTRACT

A configurable electrode instrument for use in loop electrical excision procedures for removal of damaged tissue by allowing for a peeling of the epithelium of the ectocervix rather than a deep stromal excision. The instrument has an elongate main body member with an endocervical portion contiguous to, integrally connected to and extending therefrom. A contact portion extends from the elongate main body member for operative engagement with an electro-surgical device. The endocervical portion has a laterally oriented stop arm contiguous to the elongate main body member and a longitudinal member extending from the stop arm and elongate main body member. The stop arm limits the depth of insertion of the endocervical portion into an endocervix. The stop arm is hingedly connected to the elongate main body member. An electrode extends generally diagonally from near an end of the stop arm to near an outer end of the longitudinal member, the electrode being in electrical communication through the endocervical portion, the elongate main body member and the contact portion so as to electrically connect with the electro-surgical device. Adjustment for the rotational angle of the stop arm is provided for varying the configuration of the electrode from a generally minimally concave configuration to a substantially concave configuration.

6 Claims, 7 Drawing Sheets

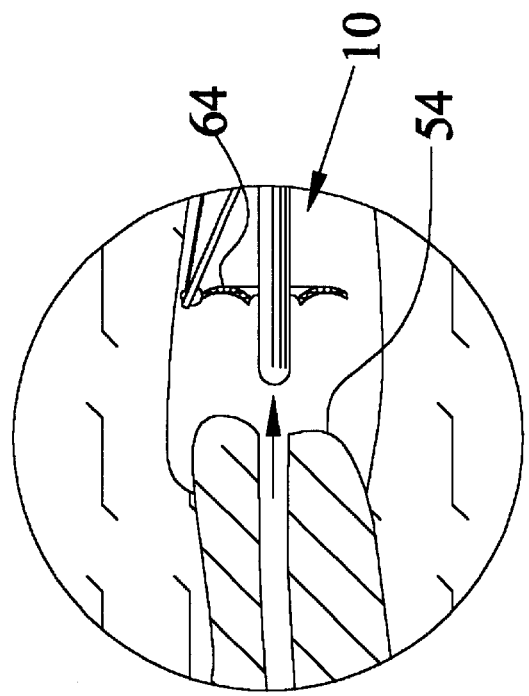
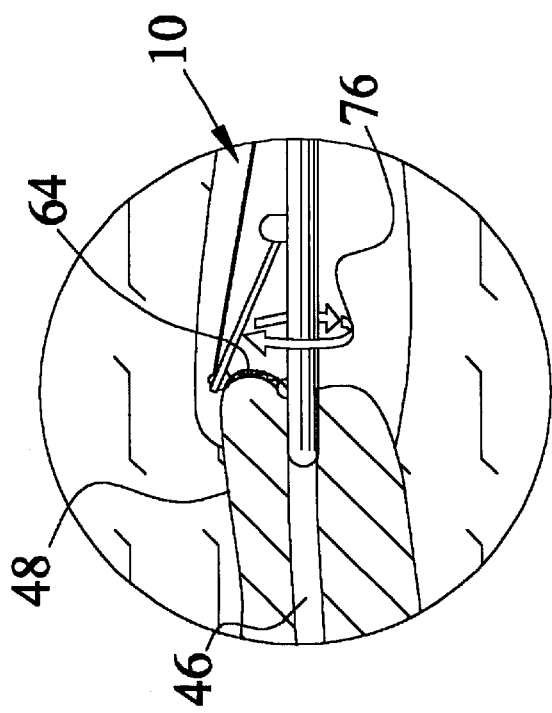
Fig. 8
Fig. 9

CONFIGURABLE ELECTRODE INSTRUMENT FOR USE IN LOOP ELECTRICAL EXCISION PROCEDURES

BACKGROUND OF THE INVENTION

1. Field of the invention.

The invention relates to an electro-surgical excisor used for excising a tissue specimen from the transformation zone of the uterine cervix.

2. Description of related art.

Using loop electrodes on the end of a handle for excising tissue from an organ, particularly the cervix, has been known in the art. However, most devices are limited in the control of the removal of damaged tissue.

Known related art includes an instrument for electro-surgical excision of the transformation zone of the uterine cervix depicted in U.S. Pat. No. 5,554,159 to Fischer. The electrode does incorporate a stop arm for control the depth of the entry of the endocervical portion of the instrument; however, the electrode is fixed at each end and extends in a straight line diagonally between the stop arm and the endocervical portion end. This instrument thereby excises a conically shaped portion of the organ and does not take into account the unique cervical shape of the individual. As such, it is likely that too much stroma or depth of the-organ undergoing the Loop Electrical Excision Procedure (LEEP) can be taken. The gross excision of the transformation zone, extra ectocervix and unnecessary stroma can result in excessive scarring, incompetent cervix and cervical stenosis. In addition, longer recovery periods and unnecessary discomfort for the patient are experienced as a result of using prior art instruments.

What is then needed is a device which is deformable concavely to conform to the unique shape of an individual's cervix or organ, thereby allowing for the excision of the minimal amount of organ tissue. This can be accomplished by an instrument that peels away the epithelium leaving stroma substantially intact, thereby promoting faster recovery, less discomfort and alleviating unnecessary scarring and other problems associated with the use of prior art instruments.

SUMMARY OF THE INVENTION

The present invention is a configurable electrode instrument for use in loop electrical excision procedures. The invention comprises an elongate main body member having a distal end and a proximal end; the distal end of the elongate main body member further having an endocervical portion contiguous to and integrally connected to said distal end and extending therefrom.

The proximal end of the elongate main body member further has a contact portion connected to the elongate main body member and extending therefrom for operative engagement with an electro-surgical device and/or manipulator or connection. The endocervical portion has a laterally-oriented stop arm contiguous to the distal end of the elongate main body member and a longitudinal member extending from the stop arm and distal end of the elongate main body member, the stop arm for limiting the depth of insertion of the endocervical portion into an endocervix.

The stop arm has a first end hingedly connected at the distal end of the elongate main body member. An electrode extends generally diagonally from near a second end of the stop arm to near an outer end of the longitudinal member. The electrode is in electrical communication through the endocervical portion, the elongate main body member and the contact portion so as to electrically connect with the electro-surgical device.

Adjustment means for adjusting a rotational angle of the stop arm about its first end are provided. The adjusting means enables the configuration of the electrode to be varied from a generally minimally concave configuration to a substantially concave configuration. The electrode can be adjusted to be configured to an individual's cervical shape, thereby allowing for a peeling excision of a transformation zone of an ectocervix, while leaving the stroma substantially intact.

The adjustment means is operatively engaged with the elongate main body member. This can be done with a manipulation member engaged with the elongate main body member which can used by the surgeon to make the necessary adjustments to form the electrode in the desired concave configuration. A linking member connects the second end of the stop arm to the manipulation member. When a surgeon wants to configure the electrode so as to obtain more concaveness, the surgeon would simply adjust the manipulation member so as to advance the linking member toward the endocervical portion, thereby rotating the free end of the stop arm toward the cervix. Similarly, if less concaveness of the electrode was desired, then the surgeon would adjust the manipulation member to retract it along the elongate main member, thereby rotating the free end of the stop arm away from the cervix.

There are several optional ways of providing the adjusting means, although a preferred method which would provide for generally infinite adjustments, is the incorporation of a concentric threaded nut around manipulation member and elongate main member, wherein when a surgeon rotates the nut, the manipulation member, which is slidingly engaged with the elongate main member, slides back and forth.

The elongate main body member is dimensioned to extend outwardly of a vaginal canal when the endocervical portion is inserted into the endocervix. In addition, the manipulation member is located such that it too extends outside the vaginal canal such that the electrode instrument, including the manipulation member may be manipulated externally of the vaginal canal by the surgeon.

The electrode is fastened to the endocervical portion at a point spaced inwardly from the outer end of the longitudinal member, and the opposite end of the electrode is fastened proximate the free end of the stop arm.

BRIEF DESCRIPTION OF THE DRAWINGS

For a fuller understanding of the nature and objects of the invention, reference should be made to the following detailed description, taken in connection with the accompanying drawings, in which:

FIG. 8 is an exploded diagrammatic view depicting the excision of the epithelium layer of the stroma being excised with the present invention; and FIG. 9 is an exploded diagrammatic view depicting the present invention being removed after completion of an excision.

DETAILED DESCRIPTION OF THE INVENTION

Figure 1A:
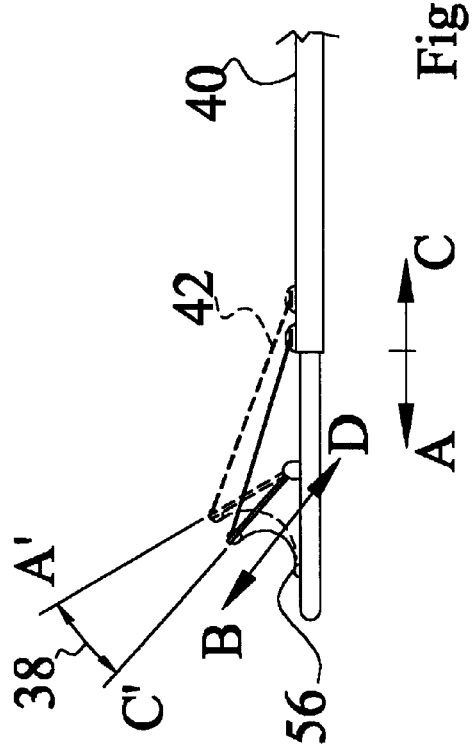
FIG. 1a is a partial exploded view of the excisor end of the invention as depicted in FIG. 1 depicting the rotation of the stop arm forming the concave shape of the electrode.
Figure 1:
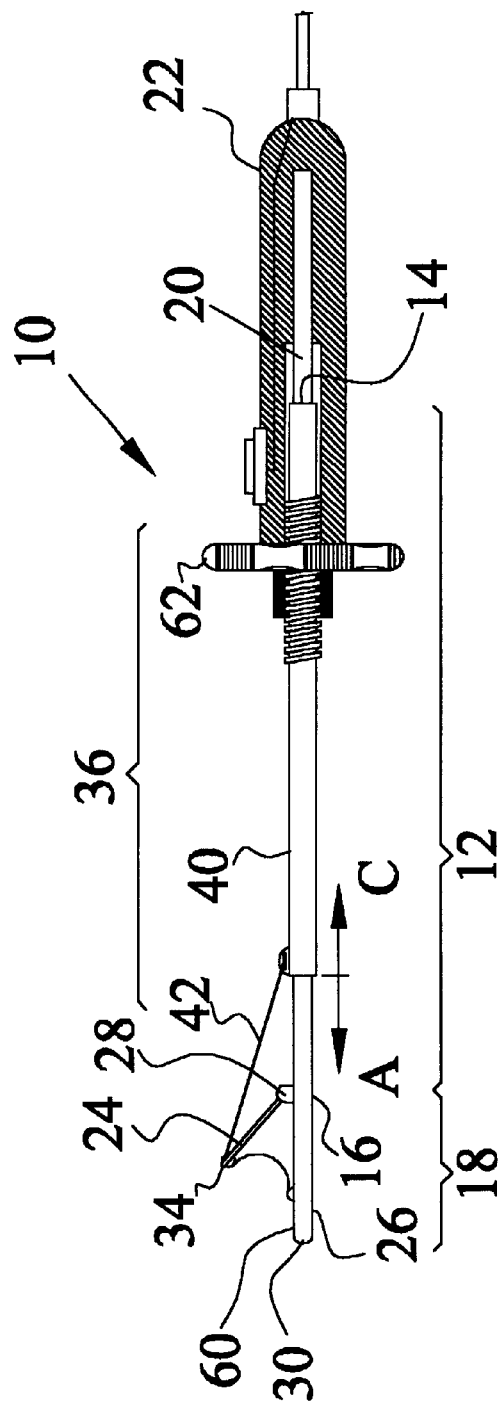
FIG. 1 is a diagrammatic view of a preferred embodiment of the present invention.

Referring now to the drawings, in particular FIGS. 1 and 1a, the invention which is a configurable electrode instrument for use in loop electrical excision procedures, depicted generally as 10, comprises an elongate main body member 12 having a distal end 16 and a proximal end 14. The distal end 16 of the elongate main body member 12 further has an endocervical portion 18 contiguous to and integrally connected to said distal end 16 and extending therefrom. FIGS. 1, 1a and 5–9 depicting the present invention are conceptual somewhat exaggerated drawings, particularly, for demonstrating the operation of the stop arm 24 and electrode 32. In reality, the stop arm is typically much shorter than that depicted and as such, is better understood with conceptual blown up drawings. Similarly, the adjustment means 36 as shown is merely a typical application of providing such adjustment features as several other means known in the art are contemplated.

Continuing with the description of the invention 10, the proximal end 14 of the elongate main body member 12 further has a contact portion 20 connected to the elongate main body member 12 and extends therefrom for operative engagement with an electro-surgical device 22.

Figure 7:
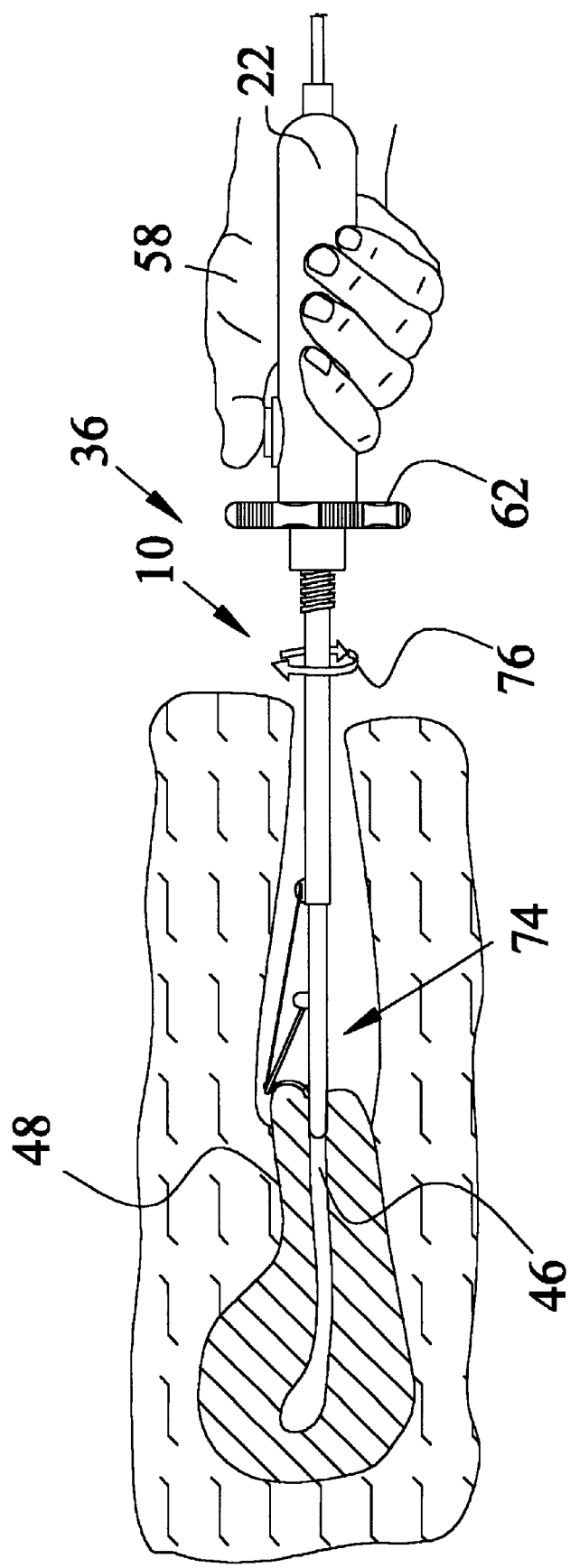
FIG. 7 is a diagrammatic view of the invention with the invention fully deployed such that the electrode is substantially shaped concavely with the shape of the transformation zone with arrows showing rotation of the excisor for tissue excision.

The endocervical portion 18 has a laterally oriented stop arm 24 contiguous to the distal end 16 of the elongate main body member 12 and a longitudinal member 26 extending from the stop arm 24 and distal end 16 of the elongate main body member 12. The stop arm 24 limits the depth of insertion of the endocervical portion 18 into the endocervix 48 as shown in FIG. 7. The stop arm 24 has a first end 28 hingedly connected at the distal end 16 of the elongate main body member 12.

An electrode 32 extends generally diagonally from near a second end 34 of the stop arm 24 to near an outer end 30 of the longitudinal member 26. The electrode 32 is in electrical communication through the endocervical portion 18, the elongate main body member 12 and the contact portion 20 so as to electrically connect with the electro-surgical device 22.

Adjustment means 36 for adjusting a rotational angle 38 of the stop arm 24 about its first end 28 are provided for varying the configuration of the electrode 32 from a generally minimally The electrode 32 can be adjusted to be configured to an individual's cervical shape, thereby allowing for a peeling excision of a transformation zone 54 of an ectocervix 44. The adjustment means 36 is operatively engaged with the elongate main body member 12.

The adjustment means typically includes a manipulation member 40 which is engaged with the elongate main body member 12. The manipulation member 40 is used by the surgeon 58 for adjusting the concaveness of the electrode 32 (see FIGS. 5–7). A linking member 42 connects the second end 34 of the stop arm 24 and the manipulation member 40.

The elongate main body member 12 is dimensioned to extend outwardly of a vaginal canal 52 (FIGS. 5–7) when the endocervical portion 18 is inserted into the endocervix 46. In addition, the manipulation member 40 also extends outside the vaginal canal 52 so that the electrode instrument 10, including the manipulation member 40, may be manipulated externally of the vaginal canal 52 by the surgeon 58.

Figure 5:
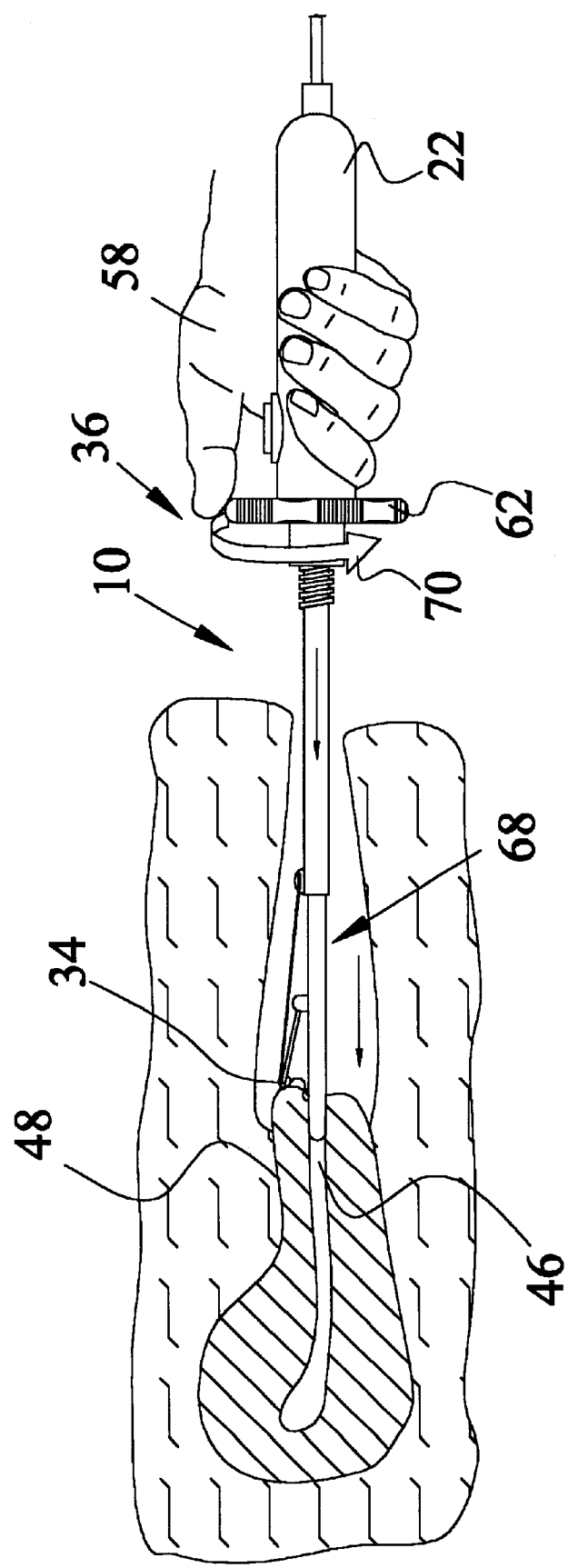
FIG. 5 is a diagrammatic view of the present invention being inserted into the vaginal canal and uterine cervix prior to deployment or forming of the concave electrode to correspond with the shape of the transformation zone, with the excisor mounted in a electro-surgical device.

As previously described herein, there are several practical applications of methods to provide adjusting means 36, although a preferred method which would provide for generally infinite adjustments, is the incorporation of a concentric threaded nut 62 around the manipulation member 40 and the elongate main member 12, wherein when a surgeon 58 rotates the nut 62 as shown by arrow 70 in FIG. 5, the manipulation member 40, which is slidingly or concentrically engaged with the elongate main member slidingly or concentrically engaged with the elongate main member 12, as shown by arrows "A" and "C" in FIGS. 1 and 1a , slides or moves back and forth. When the manipulation member 40 is caused to move in the "C" direction, linking member 42 pulls the second end 34 of the stop arm 24 back in the "A'" rotational direction, thereby lessening the degree of concavity of the electrode 32 as shown by arrow "B". Of course, the opposite is true. When the manipulation member 40 is caused to slide in the "A" direction, linking member 42 drives the second end 34 of the stop arm 24 forward in the "C'" rotational direction, thereby increasing the degree of concavity of the electrode 32 as shown by arrow "D". In other words, the desired configuration of the electrode 32 to accomplish a peeling effect is accomplished by varying the degree of concavity of the electrode 32 by causing the rotation of stop arm 24, see angle 38 in FIG. 1a.

The electrode 32 is fastened to the endocervical portion 18 at a point 56 spaced inwardly a predetermined distance 60 from said outer end 30 of the longitudinal member 26 and the opposite end of the electrode 32 is fastened proximate the free end or second end 34 of the stop arm 24.

Figure 2:
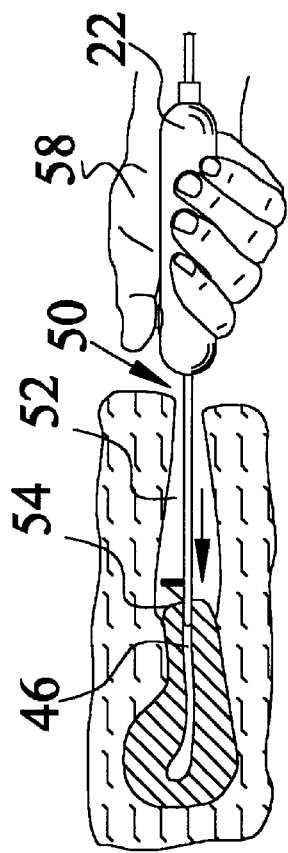
FIG. 2 is a prior art diagrammatic view of a prior art excisor being inserted into the vaginal canal and uterine cervix with the excisor. mounted in a electro-surgical device connection.
Figure 3:
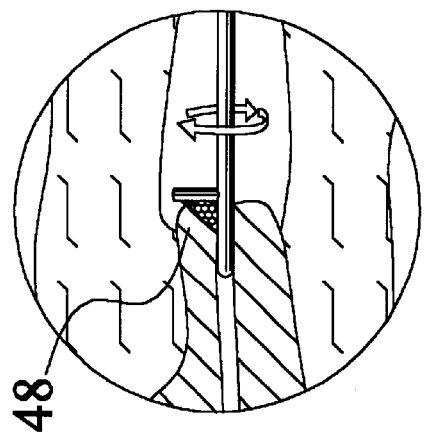
FIG. 3 is a diagrammatic side view of a portion of a prior art excisor seated into the endocervical canal with arrows showing. rotation of the excisor for tissue excision.
Figure 4:
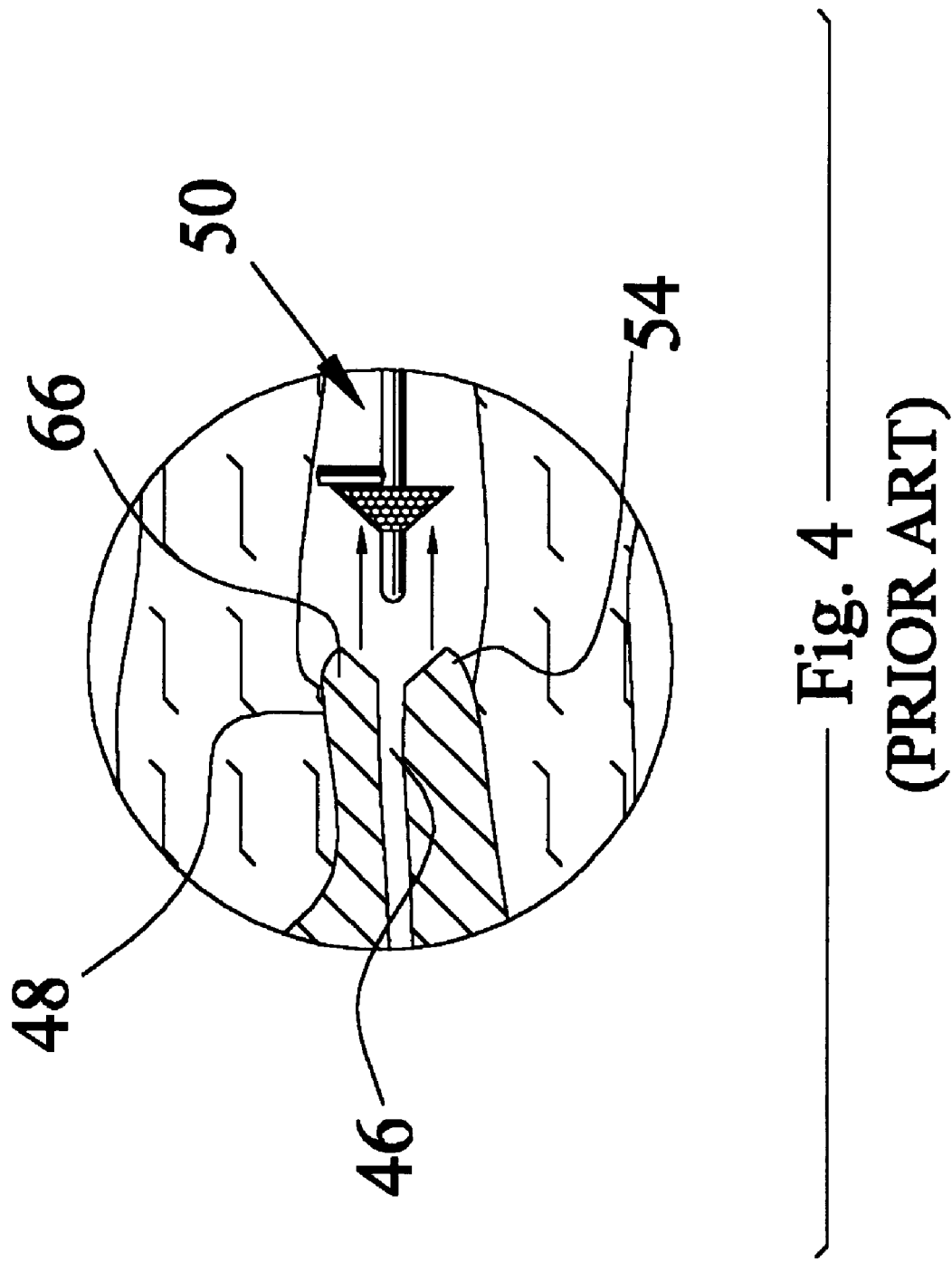
FIG. 4 is a diagrammatic view depicting a stroma removed with a prior art excisor.

To further understand the disadvantages of the prior art, a typical prior art device 50 is shown in FIGS. 2–4, wherein the diagonal electrode excises too much stroma 66 is removed due to the conical excision. The endocervical portion of the prior art instrument 50 is inserted through the vaginal canal 52 and into the endocervix 46 until the vertical stop arm engages the front of the cervix 48, at which time the electrode has entered the transformation zone 54. By rotating the instrument 50, gross excision of the stroma occurs when it is only necessary to obtain the epithelium layer 64. The present invention 10 peels away this layer and minimizes the amount stroma 66 removed so that such stroma 66 is left substantially intact.

FIGS. 5–9 diagrammatically show the present inventive instrument 10 being inserted through the vaginal canal 52. As shown in FIG. 5, the invention 10 is shown in a prior to deployment state 68, that is, the stop arm 24 second end 34 has reached the transformation zone 54. Nut 62 is then rotated as shown by arrow 70 to begin adjustment of the concaveness of the electrode 32.

Figure 6:
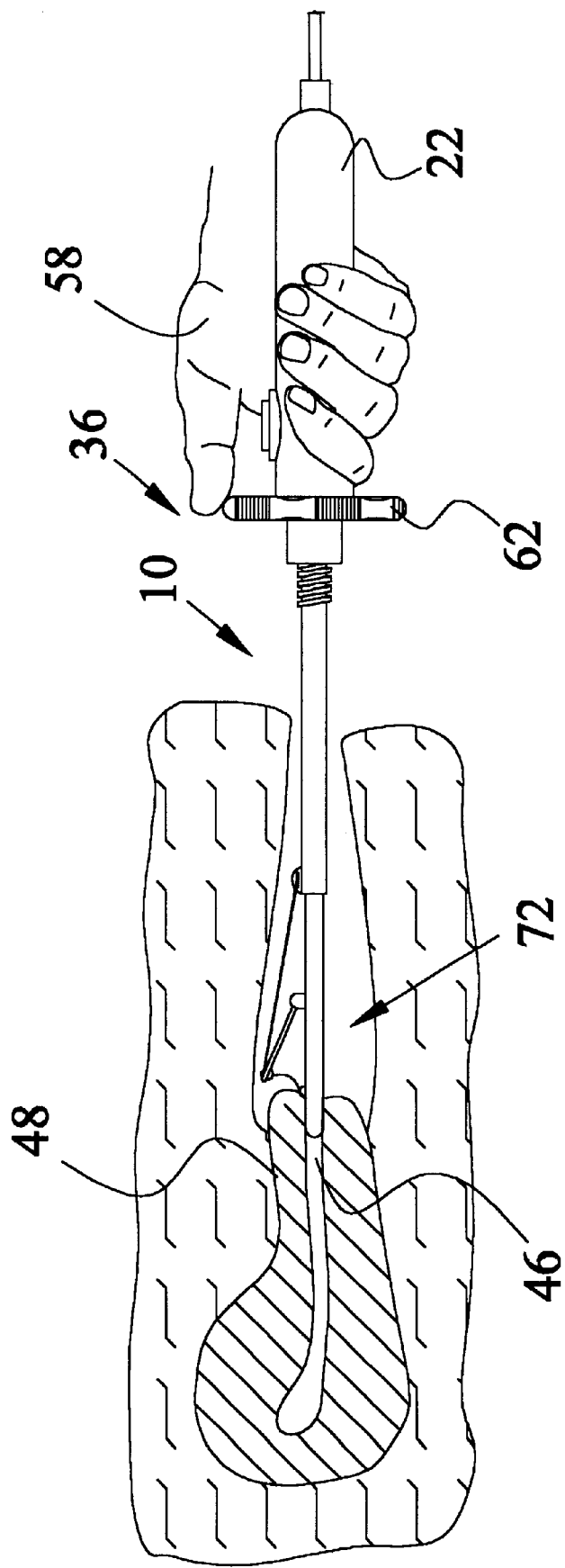
FIG. 6 is a diagrammatic side view of a portion of the present invention seated into the endocervical canal with the present invention partially deployed to form the concave electrode to correspond with the shape of the transformation zone.

Adjustment is made to obtain a desired concavity of the electrode 32 such that the shape of the electrode 32 corresponds generally to the outer shape of the cervix's transformation zone 54. FIG. 6 shows an exaggerated step, that is, a partial deployment state 72, of shaping electrode 32 to the shape of the transformation zone 54. FIG. 7 depicts a fully deployed state 74 of the present invention 10, with the electrode 32 conforming to the shape of the transformation zone 54.

Summarizing the operation of FIGS. 5–7, the electrode 32 is electrically powered by the electro-surgical device 22 and the surgeon 58 pushes the endocervical portion 18 of the present invention 10 through the endocervix or endocervical canal 46 until the second end 34 of the stop arm 24 comes into contact with the front of the cervix's transformation zone 54. The surgeon 58 then rotates the electro-surgical device 22 portion connected to the contact portion 20 of the invention 10 as shown by arrow 76 in FIGS. 7 and 8 so that the concave configured electrode 32 peels the epithelium layer 64 of the transformation zone 54, thereby leaving the stroma 66 substantially intact.

The means of fastening the electrode 32 to the endocervical portion 18 can be done in a number of ways known in the art, therefore will not be further described herein. The present invention 10 typically has a core made from an electro-conductive material which is covered by an insulating material such as a polymeric or plastic material. The stop arm 24 may be hinged in a number of ways known in the art, so long as when the linking member 42 is moved, the stop arm 24 second end 34 is caused to rotate about the hinged point 28.

As seen from the foregoing description, the present invention satisfies a long felt need to provide a device which minimizes the amount of unnecessary stroma excised in LEEP procedures, thereby essentially eliminating or at least alleviating the problems associated with the use of prior art instruments such as excessive scarring, incompetent cervix and cervical stenosis.

The invention is clearly new and useful. Moreover, it was not obvious to those of ordinary skill in this art at the time it was made, in view of the prior art considered as a whole as required by law.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in the limiting sense.

It is also to be understood that the following claims are intended to cover all of the generic and specific features of the invention herein described, and all statements of the scope of the invention which, as a matter of language, might be said to fall therebetween. Now that the invention has been described.

What is claimed is:

1. An electrode instrument for use in loop electrical excision procedures comprising:

an elongate main body member having a distal end and a proximal end, the distal end of the elongate main body member further having an endocervical portion contiguous to and integrally connected to said distal end and extending therefrom;

the proximal end of the elongate main body member further having a contact portion connected to said elongate main body member and extending therefrom for operative engagement with an electro-surgical device;

the endocervical portion having a laterally oriented stop arm contiguous to the distal end of the elongate main body member and a longitudinal member extending from the stop arm and distal end of the elongate main body member, the stop arm for limiting the depth of insertion of the endocervical portion into an endocervix;

the stop arm having a first end hingedly connected at the distal end of the elongate main body member;

an electrode extending generally diagonally from near a second end of the stop arm to near an outer end of the longitudinal member, the electrode being in electrical communication through the endocervical portion, the elongate main body member and the contact portion so as to electrically connect with the electro-surgical device; and adjustment means for adjusting a rotational angle of the stop arm about its first end, the adjusting means for varying a configuration of the electrode from a generally minimally concave configuration to a substantially concave configuration, wherein the electrode can be adjusted to be configured to an individual's cervical shape, thereby allowing for a peeling excision of a transformation zone of an ectocervix.

2. The electrode instrument according to claim 1, wherein the adjustment means is operatively engaged with the elongate main body member.

3. The electrode instrument according to claim 2, wherein the adjustment means comprises:

a manipulation member engaged with the elongate main body member, the manipulation member for adjustment by a surgeon; and a linking member connecting the second end of the stop arm and the manipulation member.

4. The electrode instrument according to claim 3, wherein the elongate main body member is dimensioned to extend outwardly of a vaginal canal when the endocervical portion is inserted into the endocervix and wherein said manipulation member is located outside the vaginal canal such that said electrode instrument, including said manipulation member may be manipulated externally of the vaginal canal by the surgeon.

5. The electrode instrument according to claim 1, wherein the electrode is fastened to said endocervical portion at a point spaced inwardly a predetermined distance from said outer end of the longitudinal member.

6. The electrode instrument according to claim 4, wherein the manipulation member is slidingly engaged with the elongate main body member.

* * * * *

UNITED STATES PATENT AND TRADEMARK OFFICE
CERTIFICATE OF CORRECTION

PATENT NO. : 6,416,513 B1
DATED : July 9, 2002
INVENTOR(S) : Scott Dresden

It is certified that error appears in the above-identified patent and that said Letters Patent is hereby corrected as shown below:

<u>Column 2,</u>
Line 61, replace "excisor. mounted in a" with -- excisor mounted in a --.

<u>Column 4,</u>
Line 32, replace "in the "C" direction," with -- in the "A" direction, --.
Line 37, replace "in the "A" direction," with -- in the "C" direction, --.

Signed and Sealed this

Nineteenth Day of November, 2002

*Attest:*

JAMES E. ROGAN
*Attesting Officer*  *Director of the United States Patent and Trademark Office*